(12) United States Patent
Kühn et al.

(10) Patent No.: US 10,856,824 B2
(45) Date of Patent: Dec. 8, 2020

(54) COOLING SYSTEM FOR AN IMAGING APPARATUS HAVING A GANTRY

(71) Applicant: Siemens Healthcare GmbH, Erlangen (DE)

(72) Inventors: Ulrich Kühn, Baiersdorf (DE); Hans-Jürgen Müller, Pretzfeld (DE); Marco Del Antonio, Fuerth (DE); Friedrich Distler, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/365,749

(22) Filed: Mar. 27, 2019

(65) Prior Publication Data

US 2019/0298286 A1    Oct. 3, 2019

(30) Foreign Application Priority Data

Apr. 3, 2018    (DE) .......................... 10 2018 204 978

(51) Int. Cl.
*H01J 35/10*    (2006.01)
*A61B 6/00*    (2006.01)
(Continued)

(52) U.S. Cl.
CPC ............ *A61B 6/4488* (2013.01); *A61B 6/035* (2013.01); *H05G 1/025* (2013.01)

(58) Field of Classification Search
CPC ....... A61B 6/035; A61B 6/4488; A61B 6/032; A61B 6/4405; A61B 6/44; A61B 6/4429; A61B 6/4441; A61B 6/4423; A61B 6/4233; A61B 6/56; A61B 2560/0406; A61B 6/4447; A61B 34/25; A61B 6/03; A61B 6/0414; A61B 6/4021; A61B 3/0041; A61B 3/0058; A61B 3/1241; A61B 6/40; A61B 6/037; A61B 6/502; A61B 2018/00005;
(Continued)

(56) References Cited

U.S. PATENT DOCUMENTS 3,650,633 A * 3/1972 Benoit .................. F04D 17/165
                                                          415/143
3,668,887 A * 6/1972 Riello ..................... F24F 13/20
                                                          62/262
(Continued)

FOREIGN PATENT DOCUMENTS

DE    10312253 A1    10/2004
DE    10304661 A1    12/2004

*Primary Examiner* — Irakli Kiknadze
(74) *Attorney, Agent, or Firm* — Harness, Dickey & Pierce, P.L.C.

(57) ABSTRACT

An embodiment of the invention relates to a cooling system for an imaging apparatus having a gantry for cooling components arranged in the gantry, including a fan and a solid body. The solid body has an inlet opening, and an outlet opening, wherein the inlet opening is larger than the outlet opening. The solid body also has a positive guide, defined by a continuous outer boundary, for a first fluid from the inlet opening to the outlet opening, which continuously transforms the geometry of the inlet opening into the geometry of the outlet opening and defines a flow path for the first fluid, and has a flow channel for a second fluid, which is arranged in heat exchange communication with the flow path, and has an inlet and an outlet for the second fluid.

17 Claims, 7 Drawing Sheets

(51) Int. Cl.
*A61B 6/03* (2006.01)
*H05G 1/02* (2006.01)

(58) Field of Classification Search
CPC ........ A61B 6/4435; H05G 1/025; H05G 1/04;
H05G 1/02; H05G 1/08; H05G 2/001;
H05G 1/06; H05G 1/085; H05G 1/10;
H05G 1/12; H05G 1/66; H02K 1/325;
H02K 3/24; H02K 3/487; H02K 3/524;
H02K 3/527; H02K 5/20; H02K 9/20;
H01J 2235/1262; H01J 35/16; H01J
2235/1216; H01J 35/105; H01J 35/18;
H01J 2235/12; H01J 2235/1287; H01J
35/101; H01J 35/106; H01J 35/12; H01J
2235/1283; H01J 2235/168; H01J
2235/081; H02J 2310/14; H02J 2310/64;
G01T 1/1648; G01T 1/2985; G01T
1/2018; G01T 7/00; G01T 1/244; G21K
1/06; G21K 1/043; G21K 1/046; A61N
2005/0652; A61N 5/0616; A61N 5/0618;
A61N 5/062
USPC .............................................. 378/4, 119, 199
See application file for complete search history.

(56) References Cited

U.S. PATENT DOCUMENTS

| | | | | |
|---|---|---|---|---|
| 4,189,281 | A * | 2/1980 | Katagiri | F04D 29/547 123/41.49 |
| 4,657,483 | A * | 4/1987 | Bede | F04D 29/545 415/210.1 |
| 4,859,140 | A * | 8/1989 | Passadore | F04D 29/464 415/48 |
| 4,948,946 | A * | 8/1990 | Fukunaga | B08B 15/04 219/230 |
| 5,000,079 | A * | 3/1991 | Mardis | F04D 29/663 361/695 |
| 5,586,861 | A * | 12/1996 | Berger | F04D 27/00 415/118 |
| 5,956,383 | A * | 9/1999 | Kendall | F04D 25/166 378/141 |
| 7,369,646 | B2 * | 5/2008 | Dittrich | H01J 35/16 378/130 |
| 7,416,333 | B2 * | 8/2008 | Zhang | F04D 29/541 378/199 |
| 2004/0202287 | A1 | 10/2004 | Muller | |
| 2004/0228450 | A1 | 11/2004 | Muller | |
| 2015/0104294 | A1 * | 4/2015 | Hustvedt | F04D 29/663 415/119 |

* cited by examiner

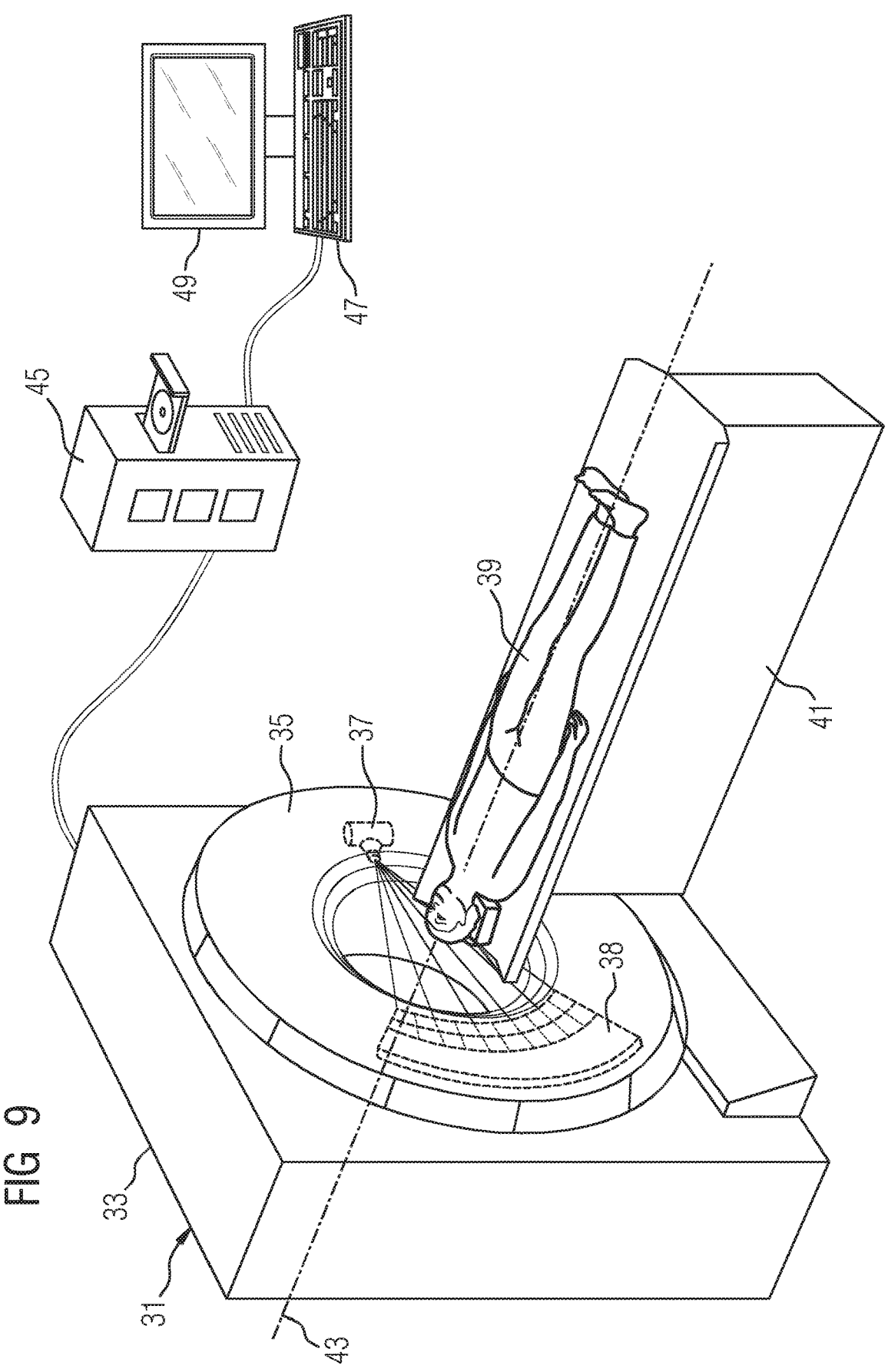

COOLING SYSTEM FOR AN IMAGING APPARATUS HAVING A GANTRY

PRIORITY STATEMENT

The present application hereby claims priority under 35 U.S.C. § 119 to German patent application number DE 102018204978.5 filed Apr. 3, 2018, the entire contents of which are hereby incorporated herein by reference.

FIELD

Embodiments of the invention generally relate to a cooling system for an imaging apparatus having a gantry for cooling the components arranged in the gantry; and to a gantry having a cooling system and an imaging apparatus.

BACKGROUND

During operation of an imaging apparatus, the components arranged in the imaging apparatus produce heat. For example, the heat produced by the system components arranged on a gantry of a computed tomography system can add up to between 10 kW and 20 kW heat during operation. This heat has to be dissipated in order to protect the components arranged in the gantry. A supply of cooling air is frequently used in this connection, wherein the heated (cooling) air is in turn cooled via a cooling system, for instance an air-fluid heat exchanger.

As a rule, conventional fluid-fluid heat exchangers, in other words also air-fluid heat exchangers, comprise a heat exchanger structure made from a material with good thermal conductivity, for example aluminum, and a fan, which provides a flow of the fluid for cooling through the heat exchanger structure. As a rule, the heat exchanger structure consists of an arrangement of pipes through which a cooling fluid is conveyed, and around which the heated fluid flows. The heated fluid emits heat to the cooling fluid. To enlarge the surface available for heat exchange, the pipes, through which the cooling fluid is conducted, are frequently connected to a large number of fins and metal sheets. Uniform through-flow, and therewith uniform utilization of the heat exchanger structure, is advantageous for good efficiency of the cooling system.

Conventional heat exchangers whose heat exchanger structure is frequently produced in a modular design from assembled and soldered or pressed pipes and metal sheets, as a rule have a cuboidal external form, which frequently is not adapted to the flow conditions caused by the fan and/or by an external construction and/or also cannot be sufficiently adapted due to the construction of the heat exchanger. Consequently, it is frequently not possible to achieve a uniform through-flow, and therewith a uniform utilization of the heat exchanger structure, and therewith efficient cooling. The result is that the cooling system, both the heat exchanger structure and the fan, is over-dimensioned.

The increasing demand for greater integration in the case of complex devices and systems means that there is also less and less installation space for the integration of cooling systems such as, for example heat exchangers.

SUMMARY

In addition, the inventors discovered that there is the added difficulty that these installation spaces can frequently have complex geometries. In the case of an imaging apparatus having a gantry, for example rounded portions or installation spaces with sections of circular segments occur. The adaptation of conventional solutions, as described above, to given installation spaces is possible to only a limited extent here.

At least one embodiment of the invention therefore discloses an improved cooling system for imaging apparatuses having a gantry. Furthermore, at least one embodiment of the invention discloses a gantry and an imaging apparatus having a cooling system of this kind.

Embodiments are directed to embodiments of an inventive cooling system for an imaging apparatus having a gantry; embodiments of an inventive gantry and embodiments of an inventive imaging apparatus. Embodiments that are advantageous and those that are inventive for themselves are the subject matter of the claims and the following description.

At least one embodiment of the invention relates to a cooling system for an imaging apparatus having a gantry for cooling components arranged in the gantry, comprising a fan and a solid body, wherein the solid body

- has an inlet opening,
- has an outlet opening, wherein the inlet opening is larger than the outlet opening,
- has a positive guide, defined by a continuous outer boundary, for a first fluid from the inlet opening to the outlet opening, which continuously transforms the geometry of the inlet opening into the geometry of the outlet opening and defines a flow path for the first fluid,
- has a flow channel for a second fluid, which is arranged in heat exchange communication with the flow path, and
- has an inlet and an outlet for the second fluid.

An embodiment of the invention also relates to a gantry of an imaging apparatus comprising an embodiment of an inventive cooling system.

For example, the gantry in an embodiment comprises a stationary part and a rotatable part which is rotatably mounted in the stationary part, with components for cooling being arranged in the rotatable part, for example an X-ray tube, or an X-ray detector opposite the X-ray tube. For example, the gantry has an exhaust duct through which heated exhaust air can be removed from the rotatable part. For example, the cooling system is fluidically coupled to the exhaust duct.

The advantages of the cooling system can also be transferred to a gantry comprising an embodiment of an inventive cooling system. More efficient cooling of the components arranged in the gantry is possible due to the more efficient design of the cooling system. The material usage, costs, space required and the noise level can be advantageously lowered also.

An embodiment of the invention also relates to an imaging apparatus comprising an embodiment of an inventive gantry.

An imaging apparatus, in an embodiment, can be for example an apparatus from the imaging modalities group comprising a computed tomography device (CT), a Single Photon Emission Computed Tomography device (SPEC-CT device) combined with a computed tomography device and a Positron Emission Tomography device combined with a computed tomography device (PET-CT device). The imaging apparatus can also have a combination of an imaging modality which is selected, for example, from the imaging modalities group, and an irradiation modality. The irradiation modality can be for example an irradiation unit for therapeutic irradiation.

An embodiment of the invention also relates to an embodiment of an inventive imaging apparatus, wherein the imaging apparatus is a computed tomography device.

BRIEF DESCRIPTION OF THE DRAWINGS

The invention will be explained below using embodiments and with reference to the accompanying figures. The depiction in the figures is schematic, highly simplified and not necessarily to scale. In the drawings:

FIG. 9 shows a schematic view of an embodiment of an inventive imaging apparatus.

DETAILED DESCRIPTION OF THE EXAMPLE EMBODIMENTS

Figure 1:
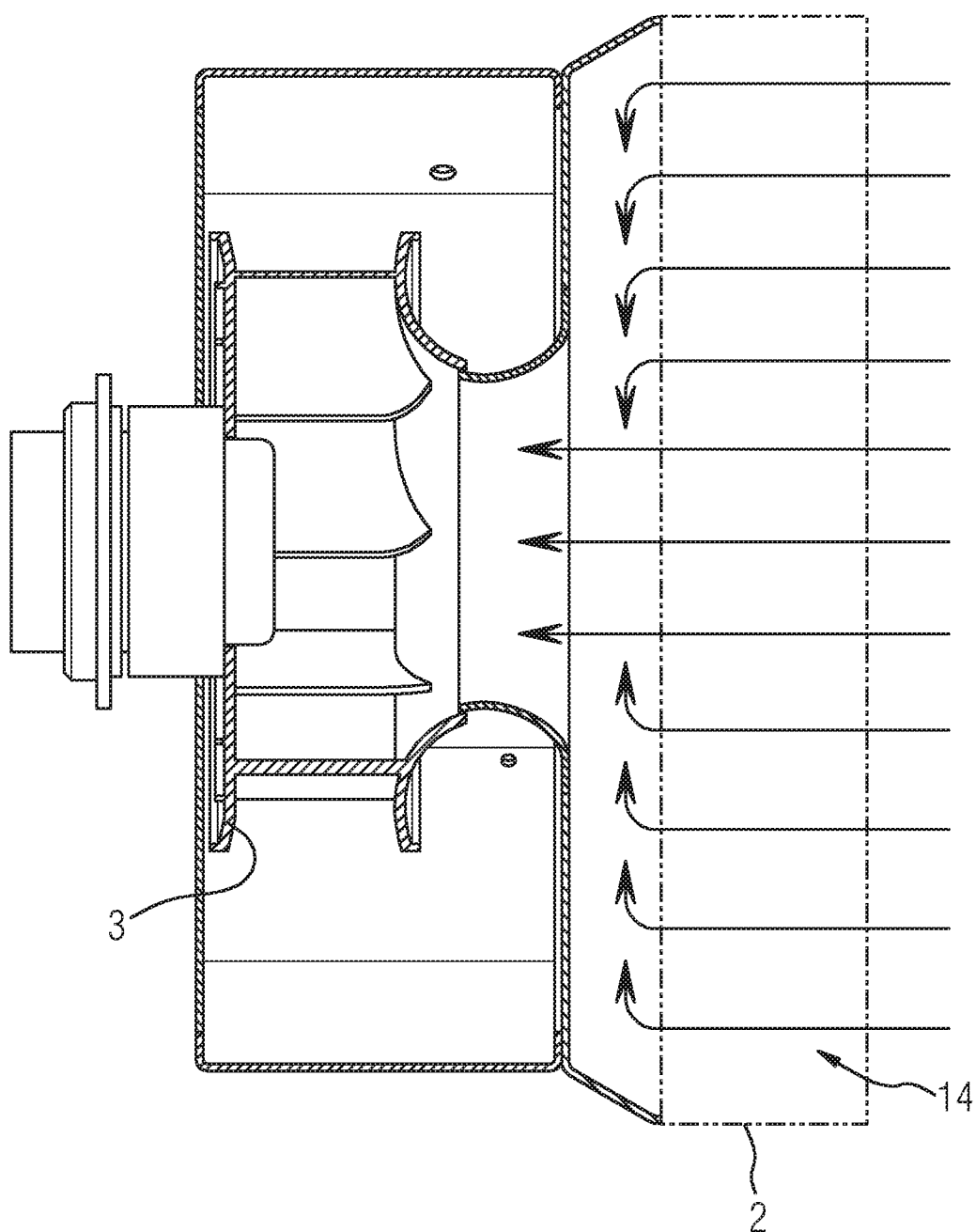
FIG. 1 shows a schematic cross-section of a conventional cooling system according to the prior art.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory.

These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the invention relates to a cooling system for an imaging apparatus having a gantry for cooling components arranged in the gantry, comprising a fan and a solid body, wherein the solid body
  has an inlet opening,
  has an outlet opening, wherein the inlet opening is larger than the outlet opening,
  has a positive guide, defined by a continuous outer boundary, for a first fluid from the inlet opening to the outlet opening, which continuously transforms the geometry of the inlet opening into the geometry of the outlet opening and defines a flow path for the first fluid,
  has a flow channel for a second fluid, which is arranged in heat exchange communication with the flow path, and
  has an inlet and an outlet for the second fluid.

At least one embodiment of the components arranged in a gantry of an imaging apparatus and which are cooled with an embodiment of the inventive cooling system can comprise, for example, an X-ray tube, which generates X-rays used for imaging, an X-ray detector and/or electronic or electrical elements.

In particular, the cooling system has a fan and a solid body. Here, a fan should essentially be taken to mean a pump for conveying a fluid. In particular, the fan can be blower or a ventilator for conveying air or a gaseous fluid. The fan can have a fan opening. The fan can also have a rotating rotor which at one side of the fan draws in the fluid for conveying and therewith causes the fluid to flow through the fan opening.

For example, the axis of rotation of the rotor, about which the rotor rotates, can run parallel or axially to the flow of air through the fan. The fan opening can have a circular design. The axis of rotation can then run, for example, through the center of the circle. Consequently, with small dimensions of the fan a high air throughput can advantageously be achieved. The fan can also have a different design, however. For example, the air can also be drawn in parallel or axially to the direction of rotation of the rotor.

The design of the fan can be freely chosen within wide ranges, provided it is capable of generating and/or assisting a flow of a fluid. The fluid conveyed by the fan can be, for example, gaseous.

A solid body is a three-dimensional body. The solid body can have an external form which is defined by the material volume taken up by the body and by cavities completely or partially enclosed by the material of the solid body. The external form can be freely chosen within wide ranges, for example it can be conical or have a form that does not taper linearly toward one side. For example, the external form can also be based on a triangular or circular area or the area of an annular segment or on different sides of the solid body. The external form can have plane and/or curved surface areas. For example, the external form can be described by a freeform surface body. The external form of the solid body can be adapted to a construction of the gantry or the imaging apparatus that surrounds the solid body or adjoins it, for example a support frame or a housing. For example, the external form can be adapted to existing installation spaces of the gantry. The external form of the solid body can advantageously be adapted to installation spaces which do not have a cuboidal geometry.

The solid body can be composed of one component or be assembled from a plurality of components. The solid body of an embodiment of the inventive cooling system is preferably one-piece.

The material, from which the solid body is produced, can be freely chosen within wide ranges, in particular provided it is strong enough to ensure the dimensional stability of the volume body. For example, the solid body is produced from one material. The solid body can also comprise different materials or even composite materials, however.

The solid body preferably comprises a material with good thermal conductivity, for example metal, for example copper or aluminum. This enables efficient heat exchange between the material of the solid body and with a substance connected to the solid body.

The solid body can also have functional elements for attaching the solid body to an external construction or for fastening other components to the solid body. For example, the solid body has a support frame, fixing points, at least one connecting element, for example dowel-like projections, or recesses for receiving at least one connecting element, such as, for example dowel-like projections or screws. The solid body can consequently be easily attached inside an external construction and with little additional constructional outlay. For example, the solid body can have reinforcements which can advantageously ensure the dimensional stability of the solid body.

The volume body can also have regions with different material density. For example, the dimensional stability of the solid body can therefore be increased in certain regions of the solid body which are exposed to higher stress, for example due to tensile forces or pressure. The solid bodies can consequently be guaranteed increased dimensional stability in case of a reduction in the material volume used.

The solid body can also have an internal design. In particular, the solid body has a positive guide, defined by a continuous outer boundary, from an inlet opening to an outlet opening for a first fluid.

The outlet opening can be facing the fan. The fan can in particular directly adjoin the outlet opening. For example, the outlet opening is circular, but can also have a different design, for example elliptical. For example, the outlet opening has a geometry adapted to the design of the fan, in particular to the fan opening. For example, both of them are circular. For example, the center of gravity of the outlet opening is located on an axis of rotation of the fan.

The inlet opening can have a geometry that is different from the outlet opening. However, it can also have the same geometry. The inlet opening can be based on a circular, triangular or rectangular area or an area with a random design. For example, the inlet opening is adapted to a flow profile of the first fluid before entry into the inlet opening. In particular, the inlet opening is larger than the outlet opening.

The solid body can also have a plurality of inlet openings and outlet openings with the same or even different geometry.

A positive guide for the first fluid essentially means that the positive guide specifies the flow path of the first fluid in the solid body from the inlet opening to the outlet opening, in other words defines a flow path for the first fluid from the inlet opening to the outlet opening.

In particular, the fan can effect and/or assist the flow of the first fluid from the inlet opening to the outlet opening along the positive guide. A continuous outer boundary can be taken to mean uninterrupted here.

The positive guide, defined by the continuous outer boundary, and the external form of the solid body can be adapted to each other, in other words the continuous outer boundary of the positive guide can essentially follow the external form and therewith have a similar geometry. For example, overall, the solid body can therefore form a funnel-like body, where both the external form and the positive guide are designed to taper to one side, in particular the side facing the fan. The geometry of the positive guide of the solid body, defined by a continuous outer boundary, and the external form of the solid body can also be designed independently of each other, however.

In an embodiment, the positive guide is inventively designed in such a way that the geometry of the inlet opening is continuously transformed into the geometry of the outlet opening. A continuous transformation can significantly reduce the occurrence of eddy currents and detachments of the first fluid and a more uniform flow can be adjusted at any point of the positive guide. Flow losses can be advantageously reduced and more efficient conveying of the first fluid inside the positive guide are therewith enabled by the fan. For example, any desired geometry of the inlet opening is continuously transformed into a circular geometry of the outlet opening. For example, the positive guide is funnel-shaped, in other words is designed to continuously taper toward the outlet opening, so the positive guide constitutes an intake funnel for the fan. A reduced pressure loss can be advantageously ensured along the defined flow path of the first fluid and a more uniform through-flow of the solid body from the inlet opening to the outlet opening is brought about by the fan. The first fluid can be advantageously efficiently conveyed by the positive guide. As a result, for example the dimensions of the fan can be reduced while retaining the same delivery volume of the first fluid.

Furthermore, the cooling system can be operated with less power, whereby the noise level can be reduced compared to the conventional solution.

In particular, the design and the course of the positive guide are based on a result of a flow simulation, and therewith an optimum uniform flow from the inlet opening to the outlet opening, and more efficient utilization of the fan can be achieved.

Inside the positive guide, the solid body can also have a structure, for example stabilizing walls or struts, which can guarantee the stability of the solid body.

The first fluid can be in the form of a gaseous or liquid phase, for example the first fluid is gaseous. In particular, the first fluid can comprise a single substance or even a mixture of substances. For example, the first fluid can comprise air.

In particular, the solid body also has a flow channel for a second fluid and an inlet and an outlet for the second fluid, through which the second fluid can be conveyed into and out of the flow channel.

In particular, the flow channel is designed in such a way that the first fluid and the second fluid do not mix together.

The flow channel is arranged in the solid body such that it is in heat exchange communication with the flow path of the first fluid in the solid body, in other words that heat can be exchanged between the first fluid in the positive guide and the second fluid, for example by way of the material of a wall of the flow channel or by way of a structure connected to the wall of the flow channel.

For example, the first fluid heat emits heat to the second fluid via the wall of the flow channel, whereby the first fluid is cooled and the second fluid is heated. However, the second fluid heat can also emit heat to the first fluid. Heat exchange can take place continuously along the flow path, defined by the positive guide, between the inlet opening and the outlet opening. As a result, a first fluid, which has a first temperature on entry into the inlet opening, can be cooled continuously along the positive guide for example and on exiting the outlet opening can have a second, lower temperature. The first fluid can accordingly have a temperature profile along the positive guide.

The walls of the flow channel preferably comprise a material with good thermal conductivity, for example a metal, for example copper or aluminum. This enables an efficient heat exchange between the second fluid flowing in the flow channel and the first fluid conveyed in the positive guide.

The flow channel can run essentially parallel to the flow path of the first fluid defined by the positive guide. The solid body can, however, also have a flow channel or a flow channel section whose alignment encloses an angle with the flow path of the first fluid.

The flow channel can also be part of a plurality of flow channels which are connected to each other. For example, flow channels that are connected to each other can form a flow channel system, with the solid body having an inlet and an outlet for the second fluid conveyed in the flow channel system. The solid body can also have two or more unconnected flow channels or two or more unconnected flow channel systems, with the solid body having at least one inlet and outlet respectively for each of the flow channels or each of the flow channel systems. For example, the entire flow of heat in the solid body can therefore advantageously be increased between the first and the second fluids and an increased heat exchange can be achieved therewith.

The flow channel or the plurality of flow channels can also be part of one or more flow circuit(s) for the second fluid, which can be partially arranged outside of the solid body.

The flow channel or the plurality of an flow channels can be directly or indirectly connected by heat-conducting connecting portions to further workpieces, preferably worked-out in a planar manner, in other words providing a large surface, which comprise a material with good thermal conductivity, for example a metal, for example copper or aluminum. For example, connecting walls can be formed between flow channels or flow channel sections or fins connected to the flow channels. The area, which is available for a heat exchange between the first fluid and the second fluid, can advantageously be increased thereby, so more efficient heat exchange is possible.

The flow channel or channels can also be arranged, for example, inside stabilizing walls of the solid body.

The arrangement, course and/or design of the flow channel or the plurality of flow channels can in particular be based on a result of a flow simulation in order to achieve improved conveying of the second fluid through the flow channels and/or an optimum distribution in the solid body and good heat exchange between the first fluid and the second fluid.

The solid body with the flow channel or flow channels and a structure potentially thermally conductively connected therewith, for example connecting walls or fins, can form a heat exchanger structure whose surface that is in contact with the first fluid conveyed through the positive guide is available for heat exchange between the first and the second fluid in the solid body. The available surface of the heat exchanger structure is advantageously optimally distributed over the solid body, so a more uniform heat exchange, and therewith more efficient utilization of the heat exchanger structure, is possible with a more uniform through-flow of the solid body by the first fluid. The heat exchanger structure can, for example, form a concentric structure around a central axis or a grid-like structure or also have a different design.

The second fluid can be in the form of a gaseous or liquid phase. For example, the second fluid is liquid. Due to the, as a rule, higher thermal capacity of liquids compared to gases, more efficient heat exchange is possible with the substance that is in contact with the liquid, for example the walls of the flow channel and a structure connected therewith, than with gaseous fluids. In particular more efficient heat exchange is consequently also possible between the first and the second fluids. In particular, the second fluid can comprise a single substance or even a mixture of substances. For example, the second fluid comprises water.

More uniform utilization of the heat exchanger structure can advantageously be achieved with an embodiment of the inventive cooling system. The heat exchange efficiency can advantageously be increased thereby. Furthermore, an increased heat exchange efficiency, the positive guide adapted to the fan-induced flow and/or the reduction in flow losses in the positive guide means that the dimensions of the fan and/or the power, with which the cooling system is operated, can be reduced. For example, the dimensions of the cooling system, the material expenditure and therewith also the weight thereof can be advantageously reduced too. Costs can be advantageously reduced thereby. The noise level can be advantageously lowered. Noise nuisance for patients or personnel operating the imaging apparatus can be avoided/reduced thereby. Overdimensioning of the cooling system can be advantageously avoided.

Improved integration of the cooling system into available installation spaces is advantageously possible, and this is not available to conventional heat exchangers. Improved integration of the cooling system into the imaging apparatus is advantageously possible thereby.

In one design of the cooling system the solid body has a plurality of delimited guide paths for the first fluid between the inlet opening and the outlet opening.

The guide paths can run along the flow path of the first fluid inside the positive guide. The delimitation between the guide paths can be uninterrupted, in other words the guide paths can be delimited from each other over the entire course of the guide paths. However, other designs of the guide paths are also possible, so the guide paths are not delimited in an uninterrupted manner. The plurality of guide paths can directly adjoin the inlet opening and end at the outlet opening, but they also can be arranged offset to the inlet and/or outlet opening, in other words for example begin only after a particular distance from the inlet opening. The guide paths can each have different designs and courses, but can in particular also be connected in parallel, in other words the flow of the first fluid in the positive guide between the inlet opening and the outlet opening can be distributed among the guide paths.

The guide paths can be delimited from each other by the design of the solid body and/or the arrangement of the flow channels and/or by structures connected to the flow channels, for example planar fins or connecting walls between the flow channels. In particular, the surface resulting due to the delimitation of the guide paths and in contact with the first fluid can be used for heat exchange. An optimally large surface can be advantageously achieved thereby for the heat exchange. The ratio between the volume of the first fluid conveyed through the positive guide to the surface of a material in contact with the volume of the first fluid can therefore also be adjusted using simple devices/elements, for example by providing more or fewer delimited guide paths in the solid body along the positive guide. The cooling capacity of the cooling system can be adjusted thereby.

For example, the guide paths are uniformly distributed in the solid body and the positive guide, for example in a grid-like manner or concentrically around a central axis. A uniform distribution of the heat exchanger structure and a more uniform heat exchange between the first and the second fluids is possible thereby. The guide paths can also be arranged in the solid body in a different way, however.

The volume flows of the first fluid along the guide paths integrated over a particular time frame can also be adjusted by way of the arrangement and design of the guide paths, so the volumes passing the guide paths within a certain time frame are adjusted via the guide paths. For example, in regions with a higher flow speed, the solid body can have narrower guide paths than in regions with a higher flow speed. A more uniform utilization of the heat exchanger structure can be advantageously enabled in this way.

In one embodiment of the cooling system, each guide path of the plurality of delimited guide paths has an input opening and an output opening and is designed in such a way that the geometry of the input opening is continuously transformed into the geometry of the output opening along the respective guide path.

With a continuous transformation, the risk of eddy currents and detachments occurring is significantly reduced and a more uniform flow with low flow losses through the guide paths can be enabled. More efficient conveying of the first fluid and more uniform utilization of the heat exchanger structure can be achieved thereby and the efficiency of the cooling system increased therewith.

In one embodiment of the cooling system the plurality of delimited guide paths is concentrically arranged around a central axis.

Concentrically means that the plurality of guide paths is arranged in an annular structure around a central axis. The annular structure can be designed to be rotationally symmetrical on rotation around the central axis. It can in particular also have a different design, however, and not have a distinguished symmetry in respect of the central axis. The central axis can correspond to a linear straight line. It can also run in a curve, however.

The central axis can preferably run through the center of gravity of the outlet opening of the solid body. The center of gravity of the outlet opening is preferably located on an axis of rotation of the fan. For example an arrangement of the guide paths adjusted to the flow conditions caused by the fan can be achieved in the positive guide thereby, so the guide paths are essentially adjusted to the flow path of the first fluid in the positive guide. A more uniform flow through the solid body and an optimum conveying capacity through the fan can be advantageously improved thereby.

For example, the flow channel or the plurality of flow channels is arranged in concentric planes around the central axis, for example within concentrically arranged walls around the central axis. A uniform distribution of the guide paths and the flow channels inside the solid body and a uniform distribution of the flow channels relative to the guide paths can be easily enabled by a concentric arrangement. Furthermore, dimensional stability of the solid body can be better achieved.

In an advantageous embodiment of the cooling system, the solid body comprises metal.

The solid body can comprise both a metal, for example copper and/or aluminum, and a composite material which comprises metal. Good thermal conductivity of the solid body can be advantageously provided thereby. An efficient transfer of heat between the first fluid and the second fluid can be advantageously enabled thereby.

In an advantageous embodiment of the cooling system the solid body is designed in one piece.

This means structural complexity when assembling the cooling system from component parts can be avoided. For example, material and connecting parts can be saved thereby.

In an advantageous embodiment of the cooling system the solid body is produced via an additive manufacturing technology.

The solid body can be produced via an additive manufacturing technology directly on the basis of a computer-based data model from formless starting materials, for example liquids, gels or pastes, or powders or neutrally shaped starting materials, for example band-, wire- or leaf-shaped material, via chemical and/or physical processes. High variability in the design is possible thereby. Consequently a direct transfer of an optimized design based on flow simulations is also possible in manufacture from the simulation. Geometries and shapes can be advantageously achieved thereby which are not possible, or are only possible with high expenditure, by way of conventional methods, for example milling or by the assembly of component parts. Time-efficient production, including of prototypes, is advantageously possible thereby. Furthermore, resource-saving production also of complex structures and shapes is possible, wherein the shapes are highly individualized and can be adapted to the respective specific application and application conditions, for example a higher or lower required cooling capacity or the design of the geometries and their adaptation to existing installation spaces and to constructions adjoining or surrounding the cooling system.

Additive manufacturing technologies can comprise, for example, powder bed methods, solid free-form fabrication, liquid material methods and other layer manufacturing methods. A plurality of manufacturing technologies, including non-additive manufacturing technologies, can also be combined. For example, additive manufacturing methods can be combined with a milling method. In particular, additive manufacturing technologies are used which can process metal, for example laser deposition welding or a metal-powder application method.

In one embodiment of the cooling system the first or second fluid is air. For example, the cooling system can be part of a cooling air supply for an imaging device.

An embodiment of the invention also relates to a gantry of an imaging apparatus comprising an embodiment of an inventive cooling system.

For example, the gantry in an embodiment comprises a stationary part and a rotatable part which is rotatably mounted in the stationary part, with components for cooling being arranged in the rotatable part, for example an X-ray tube, or an X-ray detector opposite the X-ray tube. For example, the gantry has an exhaust duct through which heated exhaust air can be removed from the rotatable part. For example, the cooling system is fluidically coupled to the exhaust duct.

The advantages of the cooling system can also be transferred to a gantry comprising an embodiment of an inventive cooling system. More efficient cooling of the components arranged in the gantry is possible due to the more efficient design of the cooling system. The material usage, costs, space required and the noise level can be advantageously lowered also.

In an advantageous embodiment of the inventive gantry of an imaging apparatus at least one section of an outer surface of the solid body adjoins a section of an inner surface of a housing of the gantry in a planar manner.

For example, the external form of the solid body is adapted to the housing and/or the gantry construction. For example, a section of the outer surface of the solid body adjoins a section of an inner surface of the housing in a planar manner. For example, a different section of the outer surface adjoins the rounded portion of the gantry in a planar manner. For example, on one side of the solid body this results in an external contour corresponding to a negative form of a circular segment or annular segment and on a different side of the solid body, a linear contour corresponding to a straight housing wall. For example, more efficient utilization of installation spaces inside a housing of a gantry is possible thereby.

An embodiment of the invention also relates to an imaging apparatus comprising an embodiment of an inventive gantry.

An imaging apparatus, in an embodiment, can be for example an apparatus from the imaging modalities group comprising a computed tomography device (CT), a Single Photon Emission Computed Tomography device (SPEC-CT device) combined with a computed tomography device and a Positron Emission Tomography device combined with a computed tomography device (PET-CT device). The imaging apparatus can also have a combination of an imaging modality which is selected, for example, from the imaging modalities group, and an irradiation modality. The irradiation modality can be for example an irradiation unit for therapeutic irradiation.

An embodiment of the invention also relates to an embodiment of an inventive imaging apparatus, wherein the imaging apparatus is a computed tomography device.

FIG. 1 shows a schematic cross-section of an embodiment of a conventional cooling system, in particular an air-fluid heat exchanger as known from the prior art, having a fan (3), and a heat exchanger structure (2), indicated only schematically here, wherein the fan (3) brings about a flow of a first fluid, in this case air, through the heat exchanger structure (2) and the design of the heat exchanger structure and the arrangement relative to the fan (3) defines a flow path (14) of the first fluid through the heat exchanger structure to the fan opening.

As a rule, the heat exchanger structure (2) comprises an arrangement of pipes through which a second fluid is conveyed and around which the first fluid flows. Heat is exchanged by way of the material of the heat exchanger structure (2) between the first and the second fluids. As a rule, the heat exchanger structure (2) is made from a material with good thermal conductivity, for example aluminum.

In order to enlarge the area available for heat exchange, the pipes, through which the second fluid is conveyed, are frequently connected to a large number of fins or metal sheets around which the first fluid likewise flows. The heat exchanger structure (2) of conventional fluid-fluid heat exchangers, which is frequently produced in a modular design from assembled and soldered or pressed pipes and metal sheets, as a rule has a cuboidal external form.

As a rule, the heat exchanger structure (2) has a design such that the flow of the first fluid is conveyed essentially horizontally through the heat exchanger structure. As a rule, the fan (3) also has a fan opening which is smaller than the area of the heat exchanger structure (2) facing it. This means that, due to the design of the heat exchanger structure (2) and of the fan (3), firstly a flow path (14) of the first fluid through the heat exchanger structure (2) to the fan (3) is defined for the first fluid, which path is different in different regions of the heat exchanger structure (2), has different path lengths and different, partially discontinuous courses. In addition, this leads to a non-uniform through-flow of the heat exchanger structure (2) with an increased volume throughput and an increased flow speed of the first fluid in the region of the overlap between fan opening and heat exchanger structure (2) and a lower volume throughput and a lower flow speed of the first fluid away from the region of the overlap between fan opening and heat exchanger structure (2). In particular, a non-uniform through-flow, and therewith a non-uniform utilization of the heat exchanger structure (2), follows thereby. In particular, an inefficient utilization of the fan (3) follows from the design of the heat exchanger structure (2) and the arrangement of the heat exchanger structure (2) relative to the fan (3). In particular, this results in an inefficient cooling capacity of the cooling system. In particular, this can to overdimensioning of both the fan (3) and the heat exchanger structure (2). In particular, the design of the conventional solution may only be adapted to a limited extent to the constructions and installation spaces surrounding or adjoining the cooling system.

Figure 2:
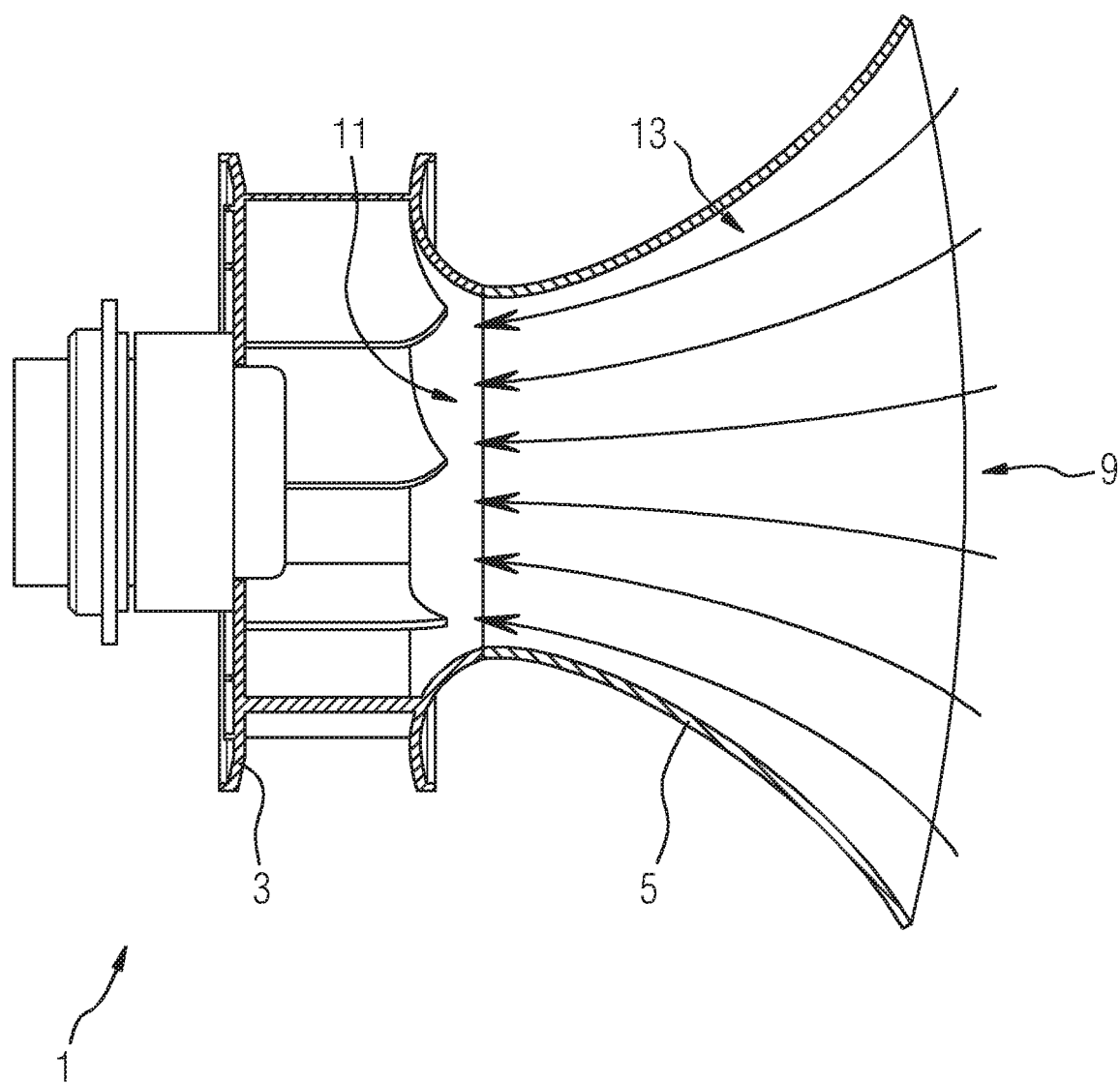
FIG. 2 shows a schematic cross-section of an inventive cooling system according to one embodiment.

FIG. 2 shows a schematic and simplified cross-section through an embodiment of an inventive cooling system (1) having a fan (3) and a solid body (5). In this diagram the solid body (5) is shown only by way of an external wall of the solid body (5). The solid body can, however, in particular also have an inner design, for example guide paths or channels, which are not shown in this simplified diagram. The solid body (5) has an inlet opening (9) for the ingress of a first fluid and an outlet opening (11) for the egress of the first fluid from the solid body (5). The inlet opening (9) is larger than the outlet opening (11). In particular, the geometry of the outlet opening (11) is adapted to the fan opening in the illustrated embodiment. In particular, the fan (3) directly adjoins the outlet opening (11) of the solid body (5). In other embodiments the fan (3) can also not adjoin the outlet opening (11).

In the illustrated embodiment the solid body (5) has an external form which has a funnel-shaped design. In other embodiments the external form can also have a different design. The fan (3) causes and/or assists a flow of a first fluid by a positive guide defined continuous outer boundary, indicated by the illustrated external wall of the solid body (5), through the solid body (5) from the inlet opening (9) to the outlet opening (11). The geometry of the inlet opening (9) is continuously transformed into the geometry of the outlet opening (11) and defines a flow path (13) for the first fluid through the solid body (5). The illustrated diagram shows, by way of example, the flow path (13) for the first fluid, resulting from a funnel-shaped positive guide, in other words continuously tapering to the outlet opening, through the solid body. In the illustrated embodiment the positive guide corresponds to an intake funnel for the fan (3), and this causes a low pressure loss along the flow path. A continuous flow path (13) of the first fluid inside the positive guide and low flow losses for the first fluid, and therewith more efficient conveying of the first fluid through the fan (3), can be advantageously achieved. The course and the path lengths of the flow path (14) and the flow speed in all regions of the positive guide can be advantageously adjusted and a more uniform through-flow achieved.

In addition, in an embodiment, the solid body inventively has at least one flow channel for a second fluid (not shown in the schematic diagram shown here), which is arranged in heat exchange communication along the flow path (13) of the first fluid. Portions of the flow channel or the flow channels are preferably arranged distributed over the solid body. More uniform through-flow of the solid body by the first fluid enables more uniform heat exchange between the first and the second fluids conveyed in the flow channels. More uniform utilization of the heat exchanger structure is advantageously possible thereby. More efficient cooling of the first fluid is possible therewith.

Figure 3:
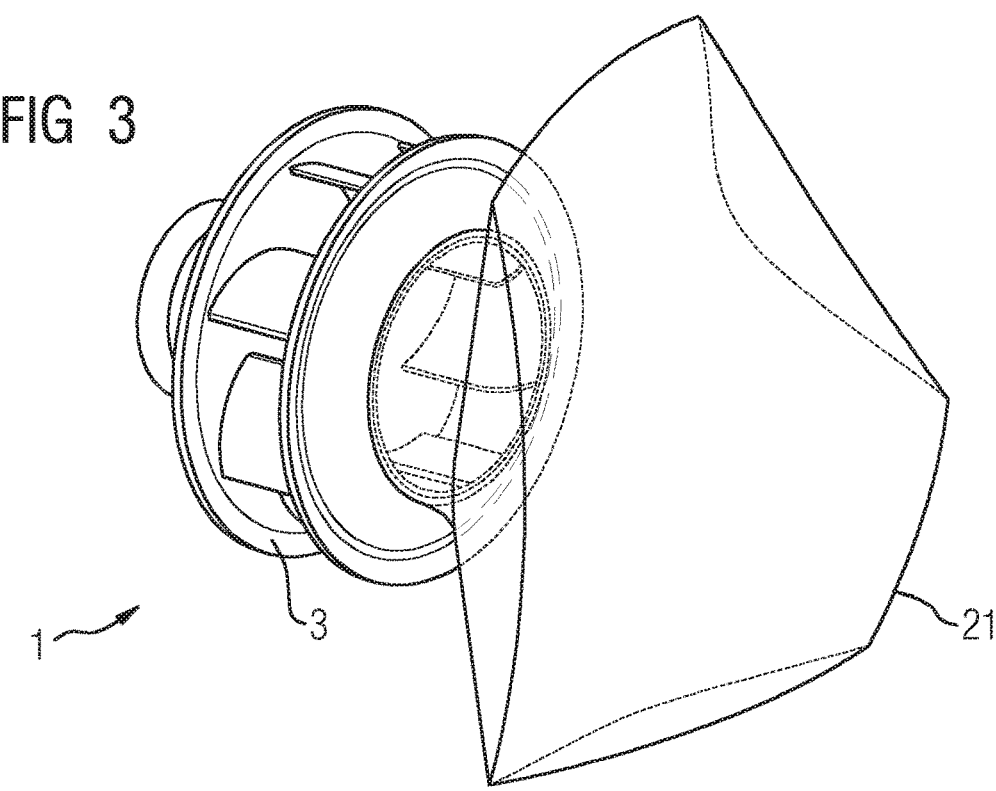
FIG. 3 shows a schematic three-dimensional view of the external form of an inventive cooling system according to one embodiment.

FIG. 3 shows a schematic three-dimensional view of the external form (21) of the solid body (5) according to one embodiment of the cooling system (1) having a fan (3) from different perspectives. The external form (21) of the solid body (5) is defined by the volume of a material taken up by the solid body and any cavities enclosed by the solid body. The three-dimensional diagram of the external form (21) of the solid body (5) in this view accordingly shows only closed surfaces and contours and, for example, no explicit inlet opening (9) or outlet opening (11). The inlet opening (9) can be, for example, a recess in one of the illustrated surfaces. In particular, the area taken up by the inlet opening can also be described by a curved surface and correspond to a region of one of the illustrated surfaces.

In the illustrated embodiment the surface of the external form (21) of the solid body (5) is a surface composite of freeform surfaces. In this embodiment the external form (21) of the solid body (5) can be described by a freeform surface body having a funnel-shaped design which is adapted thereto at the side facing the fan (3). In particular, it can also be adapted to a construction adjoining it. In this embodiment the external form of the solid body has both curved and straight contours and surfaces. For example, the external form on the one side of the solid body is therefore adapted to a rounded portion of a gantry and on a different side to a vertical housing wall of a housing of the gantry. The external form of the solid body and the design of the positive guide can be adapted to each other, in other words have a similar geometry. However, there are also embodiments in which the external form of the solid body and the design of the positive guide are not adapted to each other.

Figure 4:
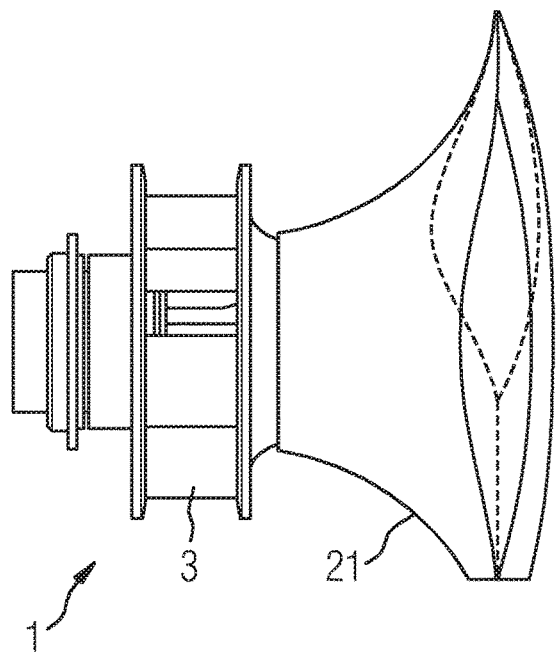
FIG. 4 shows a side view of the external form shown in FIG. 3.
Figure 5:
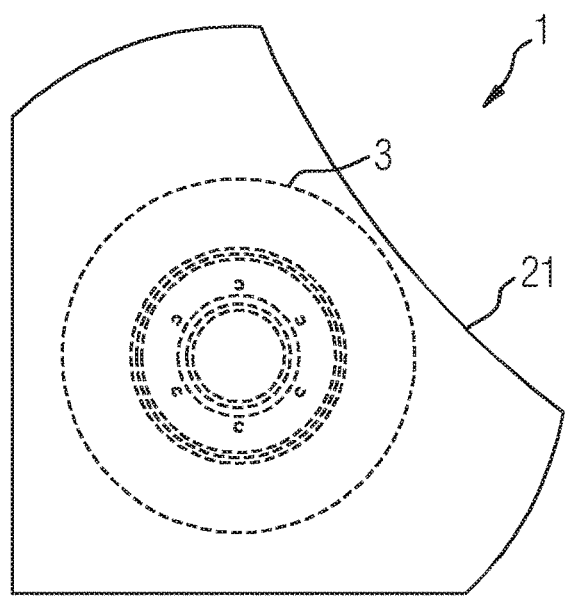
FIG. 5 shows a front view of the external form shown in FIG. 3.

For improved illustration, FIG. 4 shows a side view of the external form (21) shown in FIG. 3, having the funnel-shaped design. FIG. 5 shows a front view of the external form of the solid body (21) shown in FIG. 3, which has both curved and straight contours.

Figure 6:
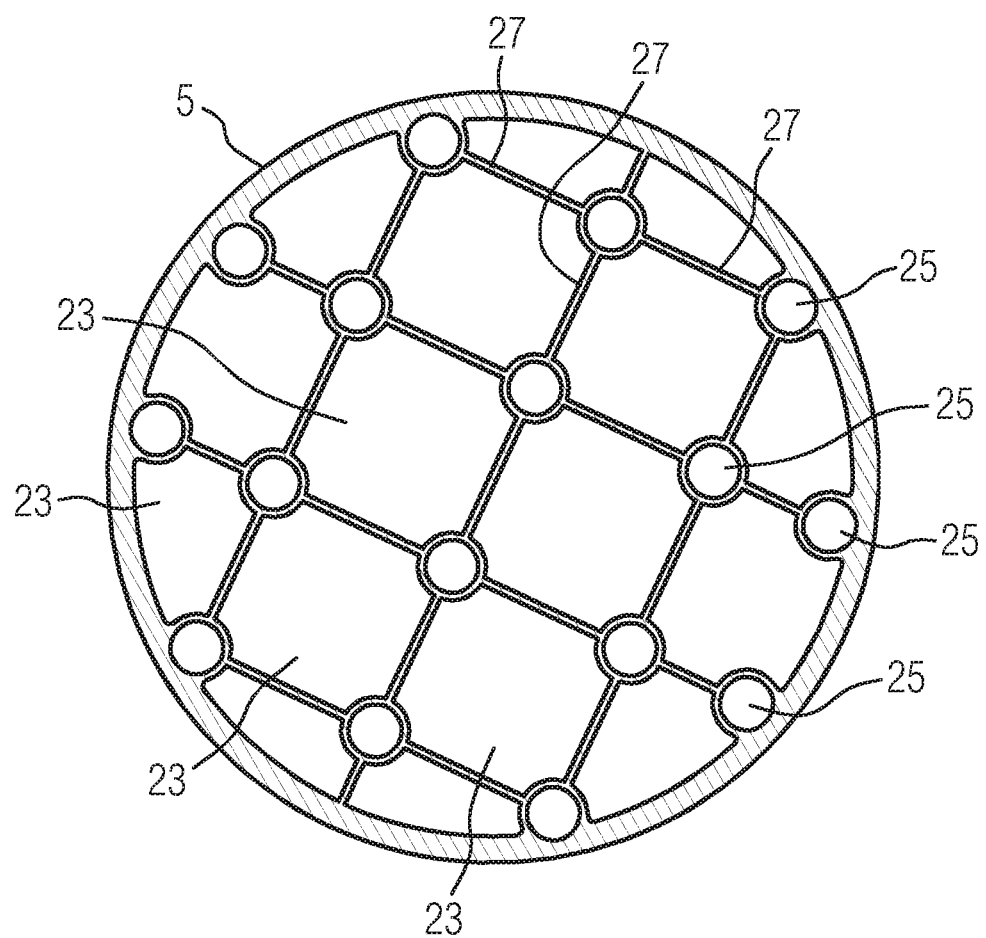
FIG. 6 shows a schematic cross-section of a solid body of an inventive cooling system having a plurality of guide paths in a first embodiment.

FIG. 6 shows a schematic cross-section through a solid body (5) of an embodiment of an inventive cooling system (1) having a plurality of delimited guide paths (23) along the positive guide between the inlet opening (9) and the outlet opening (11) according to a first embodiment of the solid body. The cross-section can correspond, for example, to a section along a plane running essentially parallel to an outlet opening (11) of the solid body (5).

In this embodiment the solid body (5) has a plurality of flow channels (25) distributed over the positive guide. In addition, the solid body (5) has connecting walls (27) arranged between the flow channels (25).

The plurality of guide paths (23) is delimited by the flow channels (25) and the connecting walls (27). The delimitation can be uninterrupted along the entire course of the guide path (23). However, embodiments in which the guide paths (23) are not delimited in an uninterrupted manner are also possible.

The cross-sectional area of a guide path (23) can vary along the course of the guide path (23) in the solid body. The cross-sectional area of a flow channel (25) can similarly vary along its course. In this embodiment the cross-sections of the plurality of flow channels are circular. A circular cross-section of a flow channel (25) advantageously offers good flow conditions for the second fluid and therewith facilitated conveying of the second fluid through the flow channel (25). In other embodiments the cross-sectional area of the flow channel (25) or the cross-sectional areas of the flow channels (25) can also have a different design, for example elliptical. The cross-sectional areas of different flow channels can have different designs.

The flow channels (25) shown in section in FIG. 6 are aligned along, in other words essentially parallel to, the flow path (13) and the delimited guide paths (23) of the first fluid. However, the illustrated embodiment of the solid body (5) and also other embodiments can also have flow channels (25) or a flow channel section (25), which are not arranged along the flow path (13). For example, these flow channels (25) or the flow channel portion (25) can also assume an angle relative to the flow path (13) and to the guide paths (23) of the first fluid. For example, in the illustrated embodiment they or it can also run parallel to the section plane shown in FIG. 6.

The walls of the plurality of flow channels (23) shown here preferably comprise a material with good thermal conductivity, for example a metal, for example aluminum or copper, or a composite material which comprises metal. This makes a good heat exchange between the second fluid conveyed in the flow channels (25) and the first fluid conveyed in the guide paths (23) possible by way of the material of the flow channel walls.

The connecting walls (27) are also arranged in heat exchange communication with the flow channels (25) and also have a material with good thermal conductivity. This makes an enlargement of the area available for heat exchange possible. A more efficient heat exchange between the first fluid and the second fluid is possible thereby. For example, more efficient cooling of the first fluid is possible.

In this embodiment all illustrated elements of the solid body (5), in other words also the walls of the flow channels (23) and the connecting walls (27), comprise the same material with good thermal conductivity. In particular, the illustrated solid body is in one piece.

Figure 7:
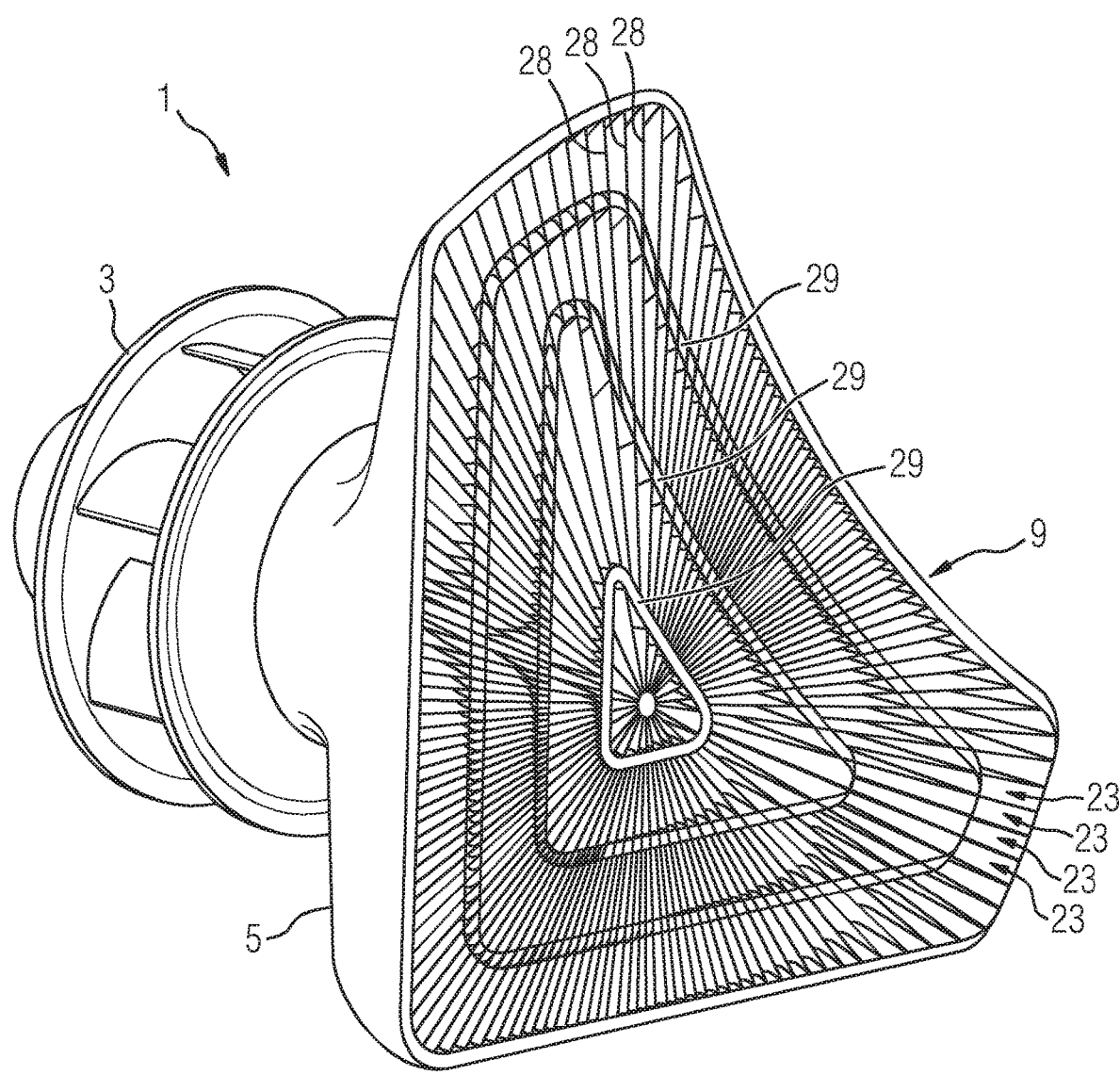
FIG. 7 shows a three-dimensional view of an inventive cooling system with a solid body having a plurality of guide paths in a second embodiment.

FIG. 7 shows a second embodiment of an inventive cooling system (1) having a solid body (5) with a plurality of guide paths (23) in a three-dimensional diagram according to a second embodiment of the solid body. FIG. 7 shows an outer view of an embodiment of the inventive cooling system (1) having a fan (3) and a solid body (5) and a plurality of guide paths (23) along the positive guide, defined by the solid body (5), between the inlet opening (9) and the outlet opening (11), wherein the outlet opening (11) adjoins the fan (3) and its geometry is adapted to the design of the fan (3). In this embodiment the external form of the solid body (5) and the design of the positive guide are adapted to each other and are funnel-shaped, in other words designed as an intake funnel for the fan (3). The external form of the solid body (5) shown here essentially matches the external form (21) illustrated in FIGS. 3 to 5.

The solid body has walls (29) arranged concentrically around a central axis. Arranged inside the concentrically arranged walls (29) is a flow channel (25) or a plurality of flow channels (25) (not visible in the diagram). In addition, the solid body (5) has fins (28) arranged between the walls and radially aligned with the central axis. The solid body (5) has thereby a plurality of delimited guide paths (23) for a first fluid, which is also arranged concentrically around the central axis. In this embodiment the central axis runs through the center of gravity of the outlet opening (11) which is also located on the axis of rotation of the fan. More efficient utilization of the fan can be achieved in this way.

The arrangement of the flow channel (25) or the plurality of flow channels (25) inside the walls (29) means, for example, that the course of the flow channel (25) or the plurality of flow channels (25) inside the concentrically arranged walls (29) can be optimized independently of the remaining structure of the solid body when producing the solid body (5).

Figure 8:
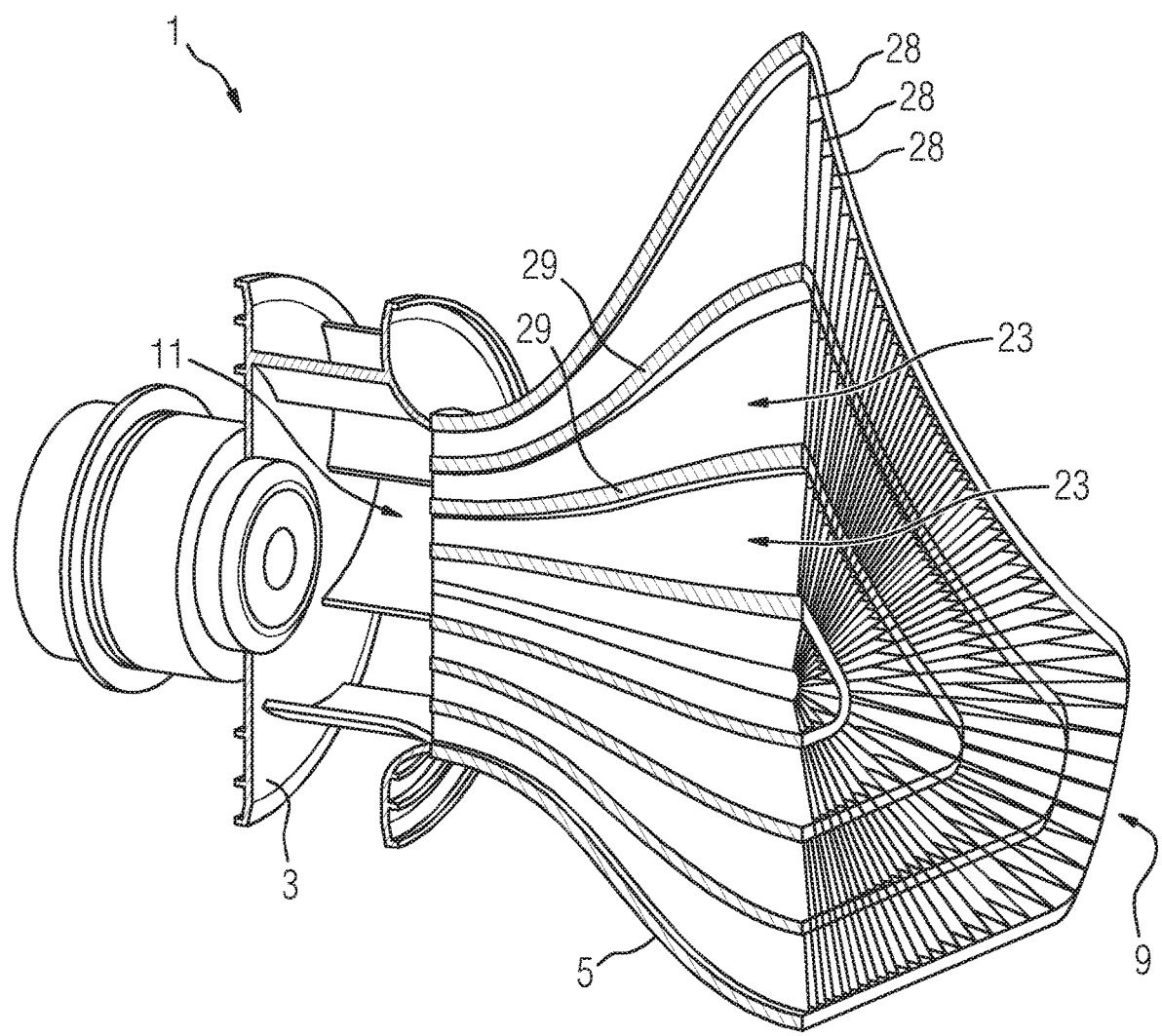
FIG. 8 shows a section through the three-dimensional view shown in FIG. 7.

FIG. 8 shows a section through the embodiment of the inventive cooling system (1) shown in FIG. 7 for improved depiction of the design of the guide paths (23) along the positive guide in the solid body (5).

The guide paths (23) have an input opening facing the inlet opening (9), defined by its outer limit due to the adjoining fins (27) and concentrically arranged walls (29) or the continuous outer boundary, and a corresponding output opening, which faces the outlet opening (11). The guide paths are deigned in such a way that the input opening of the guide paths (23) is continuously transformed into the output opening of the guide paths (23). With a continuous transformation, the occurrence of eddy currents and detachments of the first fluid can be significantly reduced and a more uniform flow can be adjusted at any point of the positive guide. Flow losses can be advantageously reduced, thereby enabling more efficient conveying of the first fluid inside the positive guide and the guide paths (23) through the fan. In this embodiment the input openings and output openings of the guide paths (23) directly adjoin the inlet opening (9) and outlet opening (11) of the solid body (5). Embodiments in which the guide paths (23) do not begin with the inlet opening (9) or end with the outlet opening (11) are also possible. The arrangement of a flow channel (25) or a plurality of flow channels (25) is provided inside the walls (29) for the second fluid (not visible in the diagram).

The concentric arrangement of the walls (29) and fins (28) enables uniform distribution of the area available for heat exchange by way of the solid body (5). The embodiment of the positive guide as an intake funnel and the embodiment of the guide paths also allows a continuous flow path of the first fluid in the positive guide and a more uniform throughflow of the solid body (5), and therewith more uniform utilization of the heat exchanger structure, and more efficient utilization of the fan (5).

FIG. 9 shows a schematic view of an embodiment of an inventive imaging apparatus comprising a gantry (31).

Without limiting the general inventive idea, a computed tomography system of at least one embodiment is shown by way of example for the imaging apparatus.

The computed tomography system includes a gantry (31) having a housing (33) and a rotor (35). The rotor (35) comprises an X-ray source (37) and an X-ray detector (38) and further components which produce heat during operation of the computed tomography system. The patient (39) is supported on the couch (41) and can be moved along the axis of rotation (43) by the gantry (31). An arithmetic unit (45) is used for controlling and calculating the sectional images. An input device (47) and an output device (49) are connected to the arithmetic unit (45).

In order to cool the components arranged in the gantry (31) the computed tomography system, not visible in this diagram, has an embodiment of an inventive cooling system (1) inside the housing. The solid body (5) of an embodiment of the inventive cooling system (1) is adapted to the construction and the installation spaces inside the housing (33) and has at least one section of an outer surface which adjoins a section of an inner surface of the housing (33) of the gantry (31) in a planar manner. This makes more efficient utilization of the existing installation spaces possible. For example, the external form of the solid body matches the external form (21) shown in FIGS. 3-5 and is adapted at the one side to the rounded portion of the gantry and at a different side to the vertical walls of the housing.

Although the invention has been illustrated in detail by the preferred exemplary embodiment, it is not limited by the disclosed examples and a person skilled in the art can derive other variations herefrom without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A cooling system for a medical imaging apparatus including a gantry for cooling components arranged in the gantry, comprising:
    a fan; and
    a solid body, the solid body including
        an inlet opening,
        an outlet opening, the inlet opening being relatively larger than the outlet opening,
        a positive guide, defined by a continuous outer boundary, for a first fluid from the inlet opening to the outlet opening, the positive guide having a continuously changing outer boundary for continuously transforming geometry of the inlet opening into geometry of the outlet opening and defining a flow path for the first fluid,
        a flow channel for a second fluid, arranged in heat exchange communication with the flow path, and
        an inlet and an outlet for the second fluid.

2. The cooling system of claim 1, wherein the solid body includes a plurality of delimited guide paths for the first fluid between the inlet opening and the outlet opening.

3. The cooling system of claim 2, wherein each guide path, of the plurality of delimited guide paths, includes an input opening and an output opening and is configured in such that, along each respective guide path, the geometry of the input opening is continuously transformed into the geometry of the output opening.

4. The cooling system of claim 3, wherein the plurality of delimited guide paths are arranged concentrically around a central axis.

5. The cooling system of claim 2, wherein the plurality of delimited guide paths are arranged concentrically around a central axis.

6. A gantry of an imaging apparatus, comprising:
    the cooling system of claim 2.

7. The gantry of claim 6, wherein at least a section of an outer surface of the solid body adjoins a section of an inner surface of a housing of the gantry in a planar manner.

8. An imaging apparatus, comprising the gantry of claim 6.

9. The cooling system of claim 1, wherein the solid body comprises metal.

10. The cooling system of claim 1, wherein the solid body is designed in one piece.

11. The cooling system of claim 1, wherein the solid body is produced via an additive manufacturing technology.

12. The cooling system of claim 1, wherein the first fluid or the second fluid is air.

13. A gantry of an imaging apparatus, comprising:
    the cooling system of claim 1.

14. The gantry of claim 13, wherein at least a section of an outer surface of the solid body adjoins a section of an inner surface of a housing of the gantry in a planar manner.

15. An imaging apparatus, comprising the gantry of claim 14.

16. An imaging apparatus, comprising the gantry of claim 13.

17. The imaging apparatus as claimed in claim 16, wherein the imaging apparatus is a computed tomography system.

* * * * *